(12) United States Patent
Black et al.

(10) Patent No.: US 10,717,719 B2
(45) Date of Patent: Jul. 21, 2020

(54) PROCESSES AND SYSTEMS FOR THE RECYCLE OF PROCESS WATER IN THE PRODUCTION OF ETHYLENE GLYCOL

(71) Applicant: SHELL OIL COMPANY, Houston, TX (US)

(72) Inventors: Jesse Raymond Black, Houston, TX (US); Roel Guillaume Hubertus Leonardus Bastings, Amsterdam (NL); Alexandre Molina, Moerdijk (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 16/092,843

(22) PCT Filed: Apr. 10, 2017

(86) PCT No.: PCT/EP2017/058522
§ 371 (c)(1),
(2) Date: Oct. 11, 2018

(87) PCT Pub. No.: WO2017/178418
PCT Pub. Date: Oct. 19, 2017

(65) Prior Publication Data
US 2019/0169154 A1 Jun. 6, 2019

(30) Foreign Application Priority Data
Apr. 12, 2016 (EP) .................................. 16164825

(51) Int. Cl.
*C07D 317/38* (2006.01)
*C07C 29/10* (2006.01)
(Continued)

(52) U.S. Cl.
CPC ........... *C07D 317/38* (2013.01); *B01D 3/007* (2013.01); *B01D 3/148* (2013.01); *B01D 53/18* (2013.01);
(Continued)

(58) Field of Classification Search
CPC ..... C07D 317/38; B01J 8/0492; B01J 8/0446; B01D 53/18; B01D 3/148; B01D 3/007; C07C 29/106; C07C 29/80; C07C 31/202
(Continued)

(56) References Cited

U.S. PATENT DOCUMENTS

| 6,184,423 B1 | 2/2001 | Jen |
| 2006/0054486 A1 | 3/2006 | Clark |
| 2017/0291119 A1 | 10/2017 | Wilkinson et al. |

FOREIGN PATENT DOCUMENTS

| EP | 0776890 A2 | 6/1997 |
| GB | 2107712 A | 5/1983 |

(Continued)

OTHER PUBLICATIONS

International Search Report and Written Opinion received for PCT Application No. PCT/EP2017/058522, dated Jun. 28, 2017, 8 pages.

*Primary Examiner* — Taylor V Oh
(74) *Attorney, Agent, or Firm* — James D. Carruth (57) ABSTRACT

Processes for producing ethylene carbonate and/or ethylene glycol, and associated reaction systems are similarly provided. Specifically, a process is provided that comprises supplying an overhead absorber stream withdrawn from an absorber to a vapor-liquid separator to yield an aqueous bottoms stream and a recycle gas stream; supplying an aqueous process stream comprising one or more impurities to a distillation apparatus to yield an overhead impurities stream and a purified aqueous process stream; supplying at least a portion of the purified aqueous process stream and an ethylene oxide product stream to the absorber; and contacting the ethylene oxide product stream with the purified aqueous process stream in the absorber in the presence of one or more carboxylation and hydrolysis catalysts to yield a fat absorbent stream comprising ethylene carbonate and/or ethylene glycol.

8 Claims, 2 Drawing Sheets

(51) Int. Cl.
  *B01D 3/00* (2006.01)
  *B01D 3/14* (2006.01)
  *B01D 53/18* (2006.01)
  *B01J 8/04* (2006.01)

(52) U.S. Cl.
  CPC ........... *B01J 8/0446* (2013.01); *B01J 8/0492* (2013.01); *C07C 29/106* (2013.01); *B01J 2208/025* (2013.01)

(58) Field of Classification Search
  USPC ....................................................... 549/230
  See application file for complete search history.

(56) References Cited

FOREIGN PATENT DOCUMENTS

| | | |
|---|---|---|
| RU | 2186053 C2 | 7/2002 |
| WO | 0226675 A2 | 4/2002 |
| WO | 2009021830 A1 | 2/2009 |
| WO | 2009140318 A1 | 11/2009 |
| WO | 2009140319 A1 | 11/2009 |
| WO | 2017102694 A1 | 6/2017 |
| WO | 2017102698 A1 | 6/2017 |
| WO | 2017102701 A1 | 6/2017 |
| WO | 2017102706 A1 | 6/2017 |

PROCESSES AND SYSTEMS FOR THE RECYCLE OF PROCESS WATER IN THE PRODUCTION OF ETHYLENE GLYCOL

CROSS REFERENCE TO RELATED APPLICATIONS

This is a national stage application of International Application No. PCT/EP2017/058522, filed 10 Apr. 2017, which claims benefit of priority to European Application No. 16164825.8, filed 12 Apr. 2016.

FIELD OF THE INVENTION

The present invention relates to processes and systems for the recycle of process water in the production of ethylene glycol.

BACKGROUND OF THE INVENTION

Ethylene glycol is a valuable industrial compound that is widely employed as starting material for the manufacture of polyester fibres and polyethylene terephthalate (PET) resins. It also finds application in automotive antifreeze and hydraulic brake fluids, aircraft de-icers as well as in pharmaceutical products.

Ethylene glycol is typically prepared from ethylene oxide, which is in turn prepared by the silver-catalyzed oxidation of ethylene. More specifically, ethylene and oxygen are passed over a silver-based epoxidation catalyst, typically at pressures of 10-30 bar and temperatures of 200-300° C., producing a product stream comprising ethylene oxide, carbon dioxide, ethylene, oxygen and water. In one well-known process, ethylene oxide is then reacted with a large excess of water in a non-catalytic process, producing a glycol product stream comprising close to 90 wt. % monoethylene glycol (MEG), the remainder being predominantly diethylene glycol (DEG), some triethylene glycol (TEG) and a small amount of higher homologues. In another well-known process, ethylene oxide is reacted with carbon dioxide in the presence of a catalyst to produce ethylene carbonate, which is subsequently hydrolyzed to provide ethylene glycol. Reaction via ethylene carbonate significantly improves the selectivity of ethylene oxide conversion to monoethylene glycol.

In the last few decades, many efforts have been directed towards the development of simplified processes and equipment for producing alkylene glycols from alkylenes, notably ethylene glycol from ethylene. For example, GB2107712 describes a process for preparing monoethylene glycol wherein the gases from the ethylene oxide reactor are supplied directly to a reactor wherein ethylene oxide is converted to ethylene carbonate or to a mixture of ethylene glycol and ethylene carbonate.

EP 0776890 describes a process wherein the gases from the ethylene oxide reactor are supplied to an absorber, wherein the absorbing solution mainly contains ethylene carbonate and ethylene glycol. The ethylene oxide in the absorbing solution is supplied to a carboxylation reactor and allowed to react with carbon dioxide in the presence of a carboxylation catalyst. The ethylene carbonate in the absorbing solution is subsequently supplied, with the addition of water, to a hydrolysis reactor and subjected to hydrolysis in the presence of a hydrolysis catalyst.

EP2178815 describes a reactive absorption process for preparing monoethylene glycol, wherein the gases from the ethylene oxide reactor are supplied to a reactive absorber and the ethylene oxide is contacted with an aqueous lean absorbent in the presence of one or more carboxylation and hydrolysis catalysts, and wherein the majority of the ethylene oxide is converted to ethylene carbonate or ethylene glycol in the absorber.

In each of these instances, considerable volumes of process water are produced. It is often desirable from an economic perspective to recycle as much of the process water as possible, for example, by recycling the process water to the ethylene oxide absorber or reactive absorber (e.g., for use as lean absorbent). Advantageously, such recycling not only reduces operating costs because it reduces the requisite amount of fresh water to be supplied to the process, but it may also reduce costs associated with disposal of the process water as waste. Further, re-use is desirable because the purging of considerable volumes of process water may also raise environmental concerns and/or disposal issues.

However, process water often contains various impurities, which are often a result of the formation of byproducts during the production of ethylene oxide, ethylene carbonate and/or ethylene glycol. For example, an overhead stream withdrawn from an ethylene oxide absorber or reactive absorber typically comprises, in addition to water, hydrocarbon impurities such as formaldehyde, acetaldehyde, etc. Additionally, organic chloride impurities may also be found in process water due to the use of organic chloride moderators in the epoxidation reaction.

If process water is recycled to the ethylene oxide absorber or reactive absorber without first removing at least a portion of these impurities, then over time, the impurities accumulate and are deleterious to the overall quality of the resulting glycol product and/or cause catalyst degradation.

U.S. Pat. No. 6,184,423 to Zo-Chun Jen discloses a process for removing acid impurities from process water in an ethylene glycol plant by utilizing anionic resins to adsorb formic acid and acetic acid from the process water. However, removal of impurities from a process water stream without the use of such resins would be advantageous from a cost standpoint. Furthermore, only acidic impurities may be removed using such resins.

Thus, the present inventors have sought to provide improved processes and systems for the production of ethylene carbonate and/or ethylene glycol. In particular, the present inventors have sought to provide processes and systems that reduce the amount of impurities in an aqueous process stream so that it may be recycled in the production of ethylene carbonate and/or ethylene glycol and have further sought to reduce the energy consumption associated with such recycling.

SUMMARY OF THE INVENTION

Accordingly, in one aspect, a process for the production of ethylene carbonate and/or ethylene glycol is provided, the process comprising:
a) supplying an overhead absorber stream withdrawn from an absorber to a vapor-liquid separator to yield an aqueous bottoms stream and a recycle gas stream;
b) supplying an aqueous process stream comprising one or more impurities to a distillation apparatus to yield an overhead impurities stream and a purified aqueous process stream;
c) supplying at least a portion of the purified aqueous process stream and an ethylene oxide product stream to the absorber; and d) contacting the ethylene oxide product stream with the purified aqueous process stream in the absorber in the presence of one or more carboxylation and hydrolysis catalysts to yield a fat absorbent stream comprising ethylene carbonate and/or ethylene glycol.

Further, in accordance with another aspect, a reaction system for the production of ethylene carbonate and/or ethylene glycol is provided, the reaction system comprising:

an absorber comprising one or more carboxylation and hydrolysis catalysts, at least two inlets and at least two outlets, wherein a first inlet of the absorber is fluidly connected to an outlet of an ethylene oxide reactor;

a vapor-liquid separator comprising an inlet and an outlet, wherein the inlet of the vapor-liquid separator is fluidly connected to a first outlet of the absorber; and a distillation apparatus comprising an inlet and an outlet, wherein the inlet of the distillation apparatus is fluidly connected to the outlet of the vapor-liquid separator and the outlet of the distillation apparatus is fluidly connected to a second inlet of the absorber.

DETAILED DESCRIPTION OF THE INVENTION

Described herein are processes and systems for the production of ethylene carbonate and/or ethylene glycol. By using the processes and systems disclosed herein, it is possible to reduce the amount of impurities present in an aqueous process stream, thereby allowing all or substantially all of the process water generated in the production of ethylene glycol to be reused. More specifically, when an aqueous process stream comprising one or more impurities is supplied to a distillation apparatus in accordance with the present disclosure, the distillation apparatus distills a majority of the impurities present in the aqueous process stream overhead and out of the process, while water and valuable glycol product is returned to the process as a purified aqueous process stream.

Accordingly, the systems and processes disclosed herein provide the advantage that the volume of waste water generated in the production of ethylene carbonate and/or ethylene glycol may be reduced, and further that impurities are not permitted to accumulate in the process and have a deleterious effect on the quality of the resulting glycol product. Additionally, by carrying out these processes in an ethylene glycol manufacturing plant, it is possible to significantly reduce the amount of fresh water required, reduce the amount of waste water produced and reduce catalyst degradation, all of which reduce operating costs.

The process of producing ethylene glycol and/or ethylene carbonate by epoxidation of ethylene and reactive absorption of ethylene oxide has been described in detail in, among others, WO2009021830, WO2009140318, WO2009140319, the disclosures of which are hereby incorporated by reference.

Typically, the epoxidation process comprises reacting, in an ethylene oxide reactor, ethylene with oxygen in the presence of an epoxidation catalyst to form ethylene oxide. In such a reaction, the oxygen may be supplied as oxygen or as air, but is preferably supplied as oxygen. Ballast gas, for example methane or nitrogen, is typically supplied to allow operation at high oxygen levels without causing a flammable mixture. Moderator, e.g. monochloroethane (ethyl chloride), vinyl chloride or dichloroethane, may be supplied for ethylene oxide catalyst performance control.

The ethylene oxide reactor is typically a multitubular, fixed bed reactor. The epoxidation catalyst preferably comprises silver and optionally promoter metals deposited on a support material, for example, alumina. The epoxidation reaction is preferably carried out at pressures of greater than 1 MPa and less than 3 Mpa and temperatures of greater than 200° C. and less than 300° C. The ethylene oxide product stream withdrawn from the ethylene oxide reactor is preferably cooled in one or more coolers, preferably with generation of steam at one or more temperature levels.

The ethylene oxide product stream from the ethylene oxide reactor, which typically comprises ethylene oxide, unreacted reactants (i.e., ethylene and oxygen), carbon dioxide, and water, is then passed to an absorber in which it is intimately contacted with lean absorbent. Typically, the lean absorbent comprises at least 20 wt % water, and preferably comprises from 20 wt % to 80 wt % water. The lean absorbent may also comprise ethylene glycol.

In the absorber, the ethylene oxide product stream is intimately contacted with the lean absorbent in the presence of one or more carboxylation and hydrolysis catalysts. If this occurs in the presence of only one catalyst, then the catalyst must promote carboxylation and hydrolysis. If this occurs in the presence of two or more catalysts, then each catalyst can promote carboxylation or hydrolysis or can promote both reactions (provided that at least one catalyst promotes carboxylation and at least one catalyst promotes hydrolysis). Preferably, the ethylene oxide product stream is contacted with lean absorbent in the presence of at least two catalysts including a first catalyst that promotes carboxylation and a second catalyst that promotes hydrolysis. Suitably, the absorber may be the sort of reactive absorber described in WO2009021830 or in co-pending application PCT/EP2015/071534.

Preferably, the one or more carboxylation and hydrolysis catalysts is/are homogenous, and the lean absorbent contains the one or more catalysts. Homogeneous catalysts that are known to promote carboxylation include alkali metal halides such as potassium iodide and potassium bromide, and halogenated organic phosphonium or ammonium salts such as tributylmethylphosphonium iodide, tetrabutylphosphonium iodide, triphenylmethylphosphonium iodide, triphenyl-propylphosphonium bromide, triphenylbenzylphosphonium chloride, tetraethylammonium bromide, tetramethylammonium bromide, benzyltriethylammonium bromide, tetrabutylammonium bromide and tributylmethylammonium iodide. Preferred homogeneous catalysts that are known to promote carboxylation include alkali metal iodides such as potassium iodide and halogenated organic phosphonium or ammonium salts such as tributylmethylphosphonium iodide, tetrabutylphosphonium iodide, triphenylmethylphosphonium iodide and tributylmethylammonium iodide.

Homogeneous catalysts that are known to promote hydrolysis include basic alkali metal salts such as potassium carbonate, potassium hydroxide and potassium bicarbonate, or alkali metal metalates such as potassium molybdate. Preferred homogeneous catalyst systems include a combination of potassium iodide and potassium carbonate, and a combination of potassium iodide and potassium molybdate.

In another embodiment, the one or more carboxylation and hydrolysis catalysts is/are heterogeneous and the heterogeneous catalyst(s) is/are contained in vertically stacked trays. Heterogeneous catalysts that promote carboxylation include quaternary ammonium and quaternary phosphonium halides immobilized on silica, quaternary ammonium and quaternary phosphonium halides bound to insoluble polystyrene beads, and metal salts such as zinc salts immobilized on solid supports containing quaternary ammonium or quaternary phosphonium groups, such as ion exchange resins containing quaternary ammonium or quaternary phosphonium groups. Heterogeneous catalysts that promote hydrolysis include metalates immobilised on solid supports, for example molybdates, vanadates or tungstates immobilised on ion exchange resins containing quaternary ammonium or quaternary phosphonium groups, or basic anions such as bicarbonate ions immobilised on solid supports, for example bicarbonate immobilised on ion exchange resins containing quaternary ammonium or quaternary phosphonium groups.

The temperature in the absorber is preferably from 50° C. to 160° C., preferably from 80° C. to 150° C., more preferably from 80° C. to 120° C. This is higher than the temperature in an absorber in a conventional process and is required to promote the carboxylation and hydrolysis reactions. Temperature higher than 160° C. is not preferred as this may reduce the selectivity of ethylene oxide conversion to ethylene glycol. Both the ethylene oxide product stream and the lean absorbent are preferably supplied to the absorber at temperatures in the range from 50° C. to 160° C.

The pressure in the absorber is from 1 to 4 Mpa, preferably from 2 to 3 Mpa. The preferred pressure is a compromise between lower pressures that require less expensive equipment (e.g. equipment having thinner walls) and higher pressures that increase absorption and reduce the volumetric flow of the gas, thereby reducing the size of equipment and piping.

At least 50% of the ethylene oxide entering the absorber is converted in the absorber. Preferably, at least 60%, more preferably at least 70%, even more preferably at least 80%, most preferably at least 90% of the ethylene oxide entering the absorber is converted in absorber. The ethylene oxide may undergo carboxylation, providing ethylene carbonate. The ethylene oxide may undergo hydrolysis, providing ethylene glycol. Additionally, the ethylene carbonate that is produced from the ethylene oxide may undergo hydrolysis, providing ethylene glycol.

The ethylene oxide product stream supplied to the absorber comprises carbon dioxide. However, it is possible that the ethylene oxide product stream may contain insufficient carbon dioxide to achieve desired levels of carboxylation. Optionally, an additional source of carbon dioxide is supplied to the absorber, e.g. recycle carbon dioxide from a finishing reactor, carbon dioxide from a carbon dioxide recovery unit or, at start-up, carbon dioxide from an external source.

A 'fat absorbent' stream is withdrawn from the absorber, preferably by withdrawing liquid from the bottom of the absorber. The fat absorbent stream will comprise ethylene carbonate and/or ethylene glycol and any remaining ethylene oxide, if present, depending on the conditions, set-up and catalyst in the absorber. In addition, when the one or more carboxylation and hydrolysis catalysts is/are homogenous, the fat absorbent stream will further comprise the one or more carboxylation and hydrolysis catalysts.

Optionally, a portion or all of the fat absorbent stream is supplied to one or more finishing reactors (e.g., to provide further conversion of any ethylene oxide and/or ethylene carbonate that was not converted to ethylene glycol in the absorber). Suitable finishing reactors may include a carboxylation reactor, a hydrolysis reactor, a carboxylation and hydrolysis reactor, and a combination thereof. Supply to one or more finishing reactors is preferred if a significant quantity (e.g. at least 1%) of ethylene oxide or ethylene carbonate is not converted to ethylene glycol in the absorber. To maximize conversion of ethylene oxide in the absorber, spraying nozzles can be employed in the sump (bottom section) of the absorber, to disperse carbon dioxide and promote carboxylation. Optionally, steam may be injected into a finishing reactor suitable for hydrolysis.

Carbon dioxide may be produced in the one or more finishing reactors and, if desired, may be separated from the one or more finishing reactor product stream(s) as it leaves the one or more finishing reactors and is optionally recycled to the absorber.

The temperature in the one or more finishing reactors is typically from 100° C. to 200° C., preferably from 100° C. to 180° C. The pressure in the one or more finishing reactors is typically from 0.1 to 3 Mpa.

The fat absorbent stream or a finishing reactor product stream is optionally supplied to a flash vessel or to a light ends stripper. Light ends are removed in the flash vessel or in the light ends stripper. (Light ends are gases such as ethylene, and also ballast gases such as methane.) Optionally, if desired, flash vaporization may be achieved in a finishing reactor (e.g., hydrolysis reactor) so that a separate flash vessel may not be required and the equipment used in the process is thereby reduced.

Optionally, a flash vessel may be located directly after the absorber so the fat absorbent stream passes directly from an outlet of the absorber to the flash vessel. When there is at least one finishing reactor, a flash vessel may be located after all of the one or more finishing reactors so that the finishing reactor product stream passes from said finishing reactors to the flash vessel. When there is more than one finishing reactor, a flash vessel may be located between the finishing reactors such that the fat absorbent stream passes from the absorber to at least one finishing reactor, then the finishing reactor product stream passes to the flash vessel and then the stream from the flash vessel passes to at least another finishing reactor. The flash can be at pressure from 0.01 to 2 Mpa, preferably from 0.1 to 1 Mpa, most preferably from 0.1 to 0.5 Mpa.

The fat absorbent stream from the absorber, or the finishing reactor product stream from one or more finishing reactors or other product stream comprising ethylene glycol is supplied to a dehydrator as a dehydrator feed stream. The dehydrator feed stream preferably comprises very little ethylene oxide or ethylene carbonate, i.e. most of the ethylene oxide or ethylene carbonate has been converted to ethylene glycol prior to supply to the dehydrator, either in the absorber or in a finishing reactor. Preferably the molar ratio of ethylene glycol to ethylene oxide and ethylene carbonate (combined) in the dehydrator feed stream is greater than 90:10, more preferably greater than 95:5, even more preferably greater than 99:1, and most preferably at 999:1. Suitably, the dehydrator feed stream may comprise 10 ppm or less of ethylene carbonate.

The dehydrator is preferably one or more columns, including at least one vacuum column, preferably operating at a pressure of less than 0.05 Mpa, more preferably less than 0.025 Mpa and most preferably about 0.0125 Mpa.

An overhead dehydrator stream, which generally comprises water and one or more impurities, is withdrawn from the dehydrator, typically at or near the top of the dehydrator. All or a portion of the overhead dehydrator stream is then supplied to the absorber, the distillation apparatus, or a combination thereof. For example, all or a portion of the overhead dehydrator stream may be combined with a purified aqueous process stream and supplied to the absorber, combined with an aqueous bottoms stream from a vapor liquid separator and supplied to the distillation apparatus as an aqueous process stream, or a combination thereof.

Further, if desired, a portion of the overhead dehydrator stream may optionally be combined with an overhead impurities stream from the vapor-liquid separator and disposed of as waste.

A dehydrator bottom stream, comprising predominantly MEG, is withdrawn from the dehydrator, typically at or near the bottom of the dehydrator, and is optionally supplied to a separator (e.g., an evaporator or a splitter) and/or to a glycol purification apparatus (e.g., a glycol purification column) to remove impurities. When a separator is used, a glycol product stream is withdrawn from the separator, typically at or near the top, and is optionally further supplied to a glycol purification apparatus. Further, a hot process stream (e.g., a catalyst recycle stream or a glycol absorbent stream) is withdrawn from the separator, typically at or near the bottom of the separator, and is optionally recycled to the absorber. In those embodiments where the one or more carboxylation and hydrolysis catalysts used is/are homogeneous catalysts, the one or more homogenous catalysts may be separated from the dehydrator bottom stream in the separator as a catalyst recycle stream and recycled to the absorber for reuse therein. Similarly, in those embodiments where the one or more carboxylation and hydrolysis catalysts used is/are heterogeneous catalysts, a glycol absorbent stream may be withdrawn from the separator and recycled to the absorber for reuse therein.

Suitably, a hot process stream, such as a catalyst recycle stream or a glycol absorbent stream, may be withdrawn from the separator, cooled and combined with a purified aqueous process stream before being recycled to the absorber. If desired, all or a portion of the heat removed from the hot process stream may be recovered and utilized via process heat integration to provide the requisite thermal energy needed in other parts of the process, as discussed further below.

Gases that are not absorbed in the absorber are removed at or near the top of the absorber and condensed to yield an overhead absorber stream, which is supplied to a vapor-liquid separator, such as a knock-out vessel, flash vessel, etc. A recycle gas stream, which typically comprises unreacted reactants (e.g., ethylene and oxygen), ballast gas (e.g., methane), carbon dioxide, etc., is withdrawn from the vapor-liquid separator, typically at or near the top. Optionally, at least a portion of the recycle gas stream withdrawn from the vapor-liquid separator is supplied to a carbon dioxide absorption column, wherein carbon dioxide is at least partially absorbed by a recirculating absorbent stream, and/or to one or more guard beds, wherein halogen-containing impurities may be at least partially absorbed by a purification absorbent, before being recycled to the ethylene oxide reactor. Suitably, the one or more guard beds may be the sort of guard beds described in co-pending applications EP15200254.9, EP15200267.1, EP15200272.1 and EP15200275.4, the disclosures of which are hereby incorporated by reference.

An aqueous bottoms stream, which generally comprises water, one or more impurities and optionally glycols, is withdrawn from the vapor-liquid separator, typically at or near the bottom, and at least a portion of the aqueous bottoms stream is then supplied to a distillation apparatus as an aqueous process stream. Optionally, if desired, a portion of the aqueous bottoms stream may bypass the distillations apparatus and be combined with a purified aqueous process stream withdrawn from the distillation apparatus and supplied to the absorber.

In accordance with the present disclosure, an aqueous process stream comprising one or more impurities is supplied to a distillation apparatus. As previously mentioned, the aqueous process stream supplied to the distillation apparatus comprises at least a portion of the aqueous bottoms stream withdrawn from the vapor-liquid separator, at least a portion of the overhead dehydrator stream withdrawn from the dehydrator, or a combination thereof. By supplying the aqueous process stream to the distillation apparatus, the amount of one or more impurities present therein is reduced via distillation.

Typically, the aqueous process stream supplied to the distillation apparatus comprises a major amount of water (i.e., an amount of water greater than or equal to 88 wt. %, for example from about 89.5 to 99 wt. %, relative to the total weight of the aqueous process stream) and a minor amount of one or more impurities (i.e., a total amount of impurities of less than 0.6 wt. %, for example from about 0.1 to 0.5 wt. %, or from 0.2 to 0.4 wt. % relative to the total weight of the aqueous process stream). Optionally, the aqueous process stream further comprises glycols (e.g., monoethylene glycol ("MEG")) in an amount up to 12 wt. %, for example from about 0.5 to 10 wt. %, relative to the total weight of the aqueous process stream.

Examples of one or more impurities that may be found in an aqueous process stream include, but are not necessarily limited to, hydrocarbon and chlorinated hydrocarbon impurities such as aldehydes, alcohols, acetals, cyclic acetals, ethers, cyclic ethers, and esters, for example formaldehyde, acetaldehyde, glycolaldehyde, propionaldehyde, 2,3-epoxy-1,4-dioxane, 1,4-dioxane, 1,3-dioxolane, 2-methyl-1,3-dioxolane, 2-methoxy ethanol, ethanol, 2-ethoxy ethanol, 2-hydroxymethyl-1,3-dioxolane, 2,2'-bis-1,3-dioxolane, 2-chloro-methyl-1,3-dioxolane, hydroxyacetone, 2-chloroethanol, glycolates, formates, lactates, acetates, propionates and a combination thereof.

Optionally, before being supplied to the distillation apparatus, at least a portion of an aqueous process stream, at least a portion of an aqueous bottoms stream withdrawn from the vapor liquid separator, or at least a portion of an overhead dehydrator stream withdrawn from the dehydrator may be supplied to a heating mechanism, such as a preheater, and/or to a flash vessel to recover light ends (e.g., ethylene and methane), which are preferably recycled to the ethylene oxide reactor after compression. For example, in one embodiment, an aqueous bottoms stream withdrawn from the vapor liquid separator and an overhead dehydrator stream withdrawn from the dehydrator are both supplied to a preheater, the aqueous bottoms stream is then supplied to a flash vessel while the overhead dehydrator stream bypasses the flash vessel, and both streams are then combined to form the aqueous process stream supplied to the distillation apparatus. In practice, the pressure of the flash vessel should be higher than the pressure of the distillation apparatus. Therefore, the flash is typically at a pressure of from 100 kPa to 270 kPa, or from 130 kPa to 220 kPa, or from 170 kPa to 210 kPa. Preferably, the thermal energy required to heat the aqueous process stream (or aqueous bottom stream or overhead dehydrator stream) is supplied via heat exchange with a hot process stream, for example, via heat exchange with a catalyst recycle stream or a glycol absorbent stream.

In the distillation apparatus, the aqueous process stream is distilled and separated into an impurities stream, which is typically condensed and withdrawn as an overhead impurities stream, and a purified aqueous process stream, which is preferably withdrawn at or near the bottom of the distillation apparatus. The purified aqueous process stream comprises water, optionally glycols, and a reduced amount of the one or more impurities, as compared to the total amount of the impurities present in the aqueous process stream supplied to the distillation apparatus. Thus, for example, if an aqueous process stream supplied to the distillation apparatus comprises a total amount of 0.3 wt. % of impurities, the purified aqueous process stream withdrawn from the distillation apparatus would comprise less than 0.3 wt. %.

The purified aqueous process stream withdrawn from the distillation apparatus is supplied to the absorber (e.g., for constituting lean absorbent). If necessary, fresh water may also be supplied to the absorber.

A distillation apparatus suitable for use herein may comprise any distillation apparatus known in the art for the separation and/or removal of an impurity from an aqueous process stream. More specifically, a suitable distillation apparatus includes any device that separates water from at least a portion of the impurities present in an aqueous process stream based on their differences in volatilities by vaporization and subsequent condensation. Suitably, the distillation apparatus may separate water and at least a portion of the impurities present in the aqueous process stream using one or more vapor-liquid equilibrium stages.

As will be appreciated by one skilled in the art, the design and operation of the distillation apparatus can depend, at least in part, on the type and concentration of impurities present in the aqueous process stream, as well as the desired composition (e.g., desired purity) of the purified aqueous process stream. In some instances, for example, with a binary component feed, analytical methods such as the McCabe Thiele method or the Fenske equation can be used to determine the number of equilibrium stages to use to achieve the desired separation. For a multi-component feed stream, simulation models can be used for both design (e.g., to determine the number of equilibrium stages needed in order to achieve the desired separation) and operation (e.g., to determine the optimum operating conditions). In addition, once the number of equilibrium stages is determined, one skilled in the art can use known design techniques to readily determine the number of separation stages (e.g., the actual number of trays or height of packing) that can be used to achieve the desired separation. Typically, a distillation apparatus suitable for use in the present disclosure may be operated in such a way as to include between 5 and 13 separation stages, more typically between 8 and 12 separation stages.

The distillation apparatus may comprise distillation trays (plates), packing, or a combination of distillation trays and packing. Examples of suitable types of distillation trays include any type of plate commonly found in distillation columns, such as sieve plates, bubble-cap plates or valve plates, among others. The distance between each tray can be substantially the same or alternatively, the distance between each tray may vary. In either configuration, the distance between each tray may be optimized to allow for the best separation of the impurities from the aqueous process stream and/or to prevent entrainment between the trays. Additionally, in embodiments using packing, the packing material can be random dumped packing such as, for example, Raschig rings, Pall rings, or Bialecki rings in metal or ceramic. The packing material can also be structured sheet-metal packing.

In embodiments where packing is employed, the total required height of packing to provide the required number of separation stages can be determined by multiplying the number of calculated equilibrium stages by the Height Equivalent to a Theoretical Plate, or HETP for that packing. The HETP is a value of the height of packing that will give the same separation as an equilibrium stage. As known to one skilled in the art, the HETP can vary depending on the type of packing selected. In some embodiments, the total height of packing can be split into one or more zones with vapor-liquid redistributors in between the zones, for example, to accommodate height limitations due to packing structural integrity. In some embodiments, packing may offer the advantage of a lower pressure drop as compared to trays, although consideration must also be given to the cost difference arising from the choice of trays versus packing.

The operating conditions within the distillation apparatus can be adjusted according to processing conditions. For example, the distillation apparatus may be operated at a wide range of pressures, ranging from sub-atmospheric (i.e., vacuum), to near atmospheric, to super atmospheric. In practice, the general operating pressure of the distillation apparatus can be selected during system design, although there is some flexibility to adjust the pressure during normal operation. The design operating pressure can range from about 60 kilopascal (kPa) to about 220 kPa, preferably from about 80 kPa to about 180 kPa, and more preferably from about 120 kPa to about 160 kPa.

The distillation apparatus may also be operated at a wide range of temperatures. In practice, the operating temperature can be selected during system design, although there can be significant variation in the temperature during operation. In some embodiments, there can be a temperature gradient present in the distillation apparatus, with the lowest temperature in the top portion and the highest temperature in the bottom portion. This gradient may be a gradual change across the column and/or various sections of the column, or may be an abrupt temperature change. For example, at an operating pressure of 150 kPa, the operating temperature of the distillation apparatus may range from about 110° C. to about 113° C. As will be readily appreciated by one skilled in the art, the operating temperature and pressure of the distillation apparatus, and the composition of the aqueous process stream supplied to the distillation apparatus, are interdependent.

The thermal energy needed for the operation of the distillation apparatus may be supplied by a heating mechanism placed internally or externally to the distillation apparatus. For example, in a preferred embodiment, a reboiler may be employed. Optionally, the reboiler may be heated with steam or alternatively, the reboiler may be heated by heat integration with a hot process stream, for example, a catalyst recycle stream or a glycol absorbent stream.

Preferably, the efficiency of removing the one or more impurities from an aqueous process stream is greater than 98%, more preferably greater than 99% and most preferably, greater than 99.5%. In addition, preferably, a purified aqueous process stream comprises less than 0.1 wt. % impurities, more preferably less than 0.06 wt. % impurities, even more preferably less than 0.05 wt. % impurities, relative to the total weight of the purified aqueous process stream.

Suitably, when an aqueous process stream comprises formaldehyde, the efficiency of removing formaldehyde from the aqueous process stream is preferably greater than 30%, more preferably greater than 35% and most preferably greater than 39%. Similarly, when an aqueous process stream comprises 2-chloroethanol, the efficiency of removing 2-chloroethanol from the aqueous process stream is preferably greater than 40%, more preferably greater than 45% and most preferably greater than 50%. Further, when an aqueous process stream comprises one or more impurities selected from acetaldehyde, 2-chloromethyl-1,3-dioxolane, 2-methyl-1,3-dioxolane and 1,4-dioxane, the efficiency of removing one or more of these impurities from the aqueous process stream is preferably greater than 98%, more preferably greater than 99%, and most preferably 100%.

In addition, preferably, a purified aqueous process stream comprises less than 0.005 wt. % formaldehyde, more preferably less than 0.003 wt. % formaldehyde, even more preferably less than 0.002 wt. % formaldehyde, relative to the total weight of the purified aqueous process stream. Similarly, a purified aqueous process stream preferably comprises less than 0.002 wt. % of one or more impurities selected from acetaldehyde, 2-chloromethyl-1,3-dioxolane 2-methyl-1,3-dioxolane, 2-chloroethanol and 1,4-dioxane, more preferably less than 0.001 wt. %, even more preferably 0 wt. %, relative to the total weight of the purified aqueous process stream.

By using the systems and processes disclosed herein, it is possible to reduce the amount of impurities present in an aqueous process stream, thereby allowing all or substantially all of the process water generated in the production of ethylene glycol to be reused. The systems and processes disclosed herein provide the advantage that the volume of waste water generated in the production of ethylene glycol may be reduced, and further that impurities are not permitted to accumulate in the process and have a deleterious effect on the quality of the resulting glycol product. Additionally, by carrying out these processes in an ethylene glycol manufacturing plant, it is possible to significantly reduce the amount of fresh water required, reduce the amount of waste water produced and reduce catalyst degradation, all of which reduce operating costs.

Figure 1:
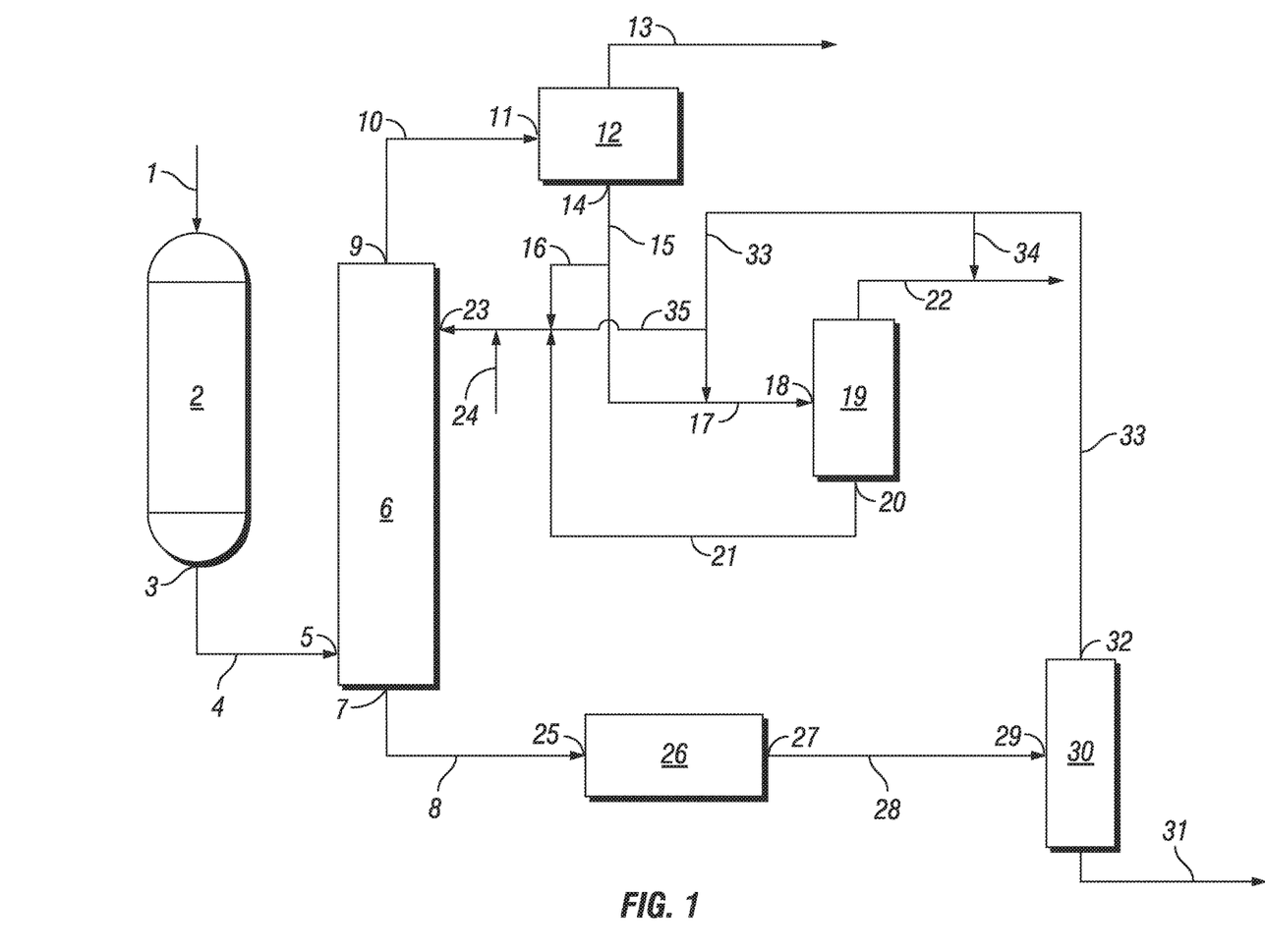
FIGS. 1 and 2 are schematic illustrations showing exemplary, but non-limiting embodiments of the present disclosure.
Figure 2:
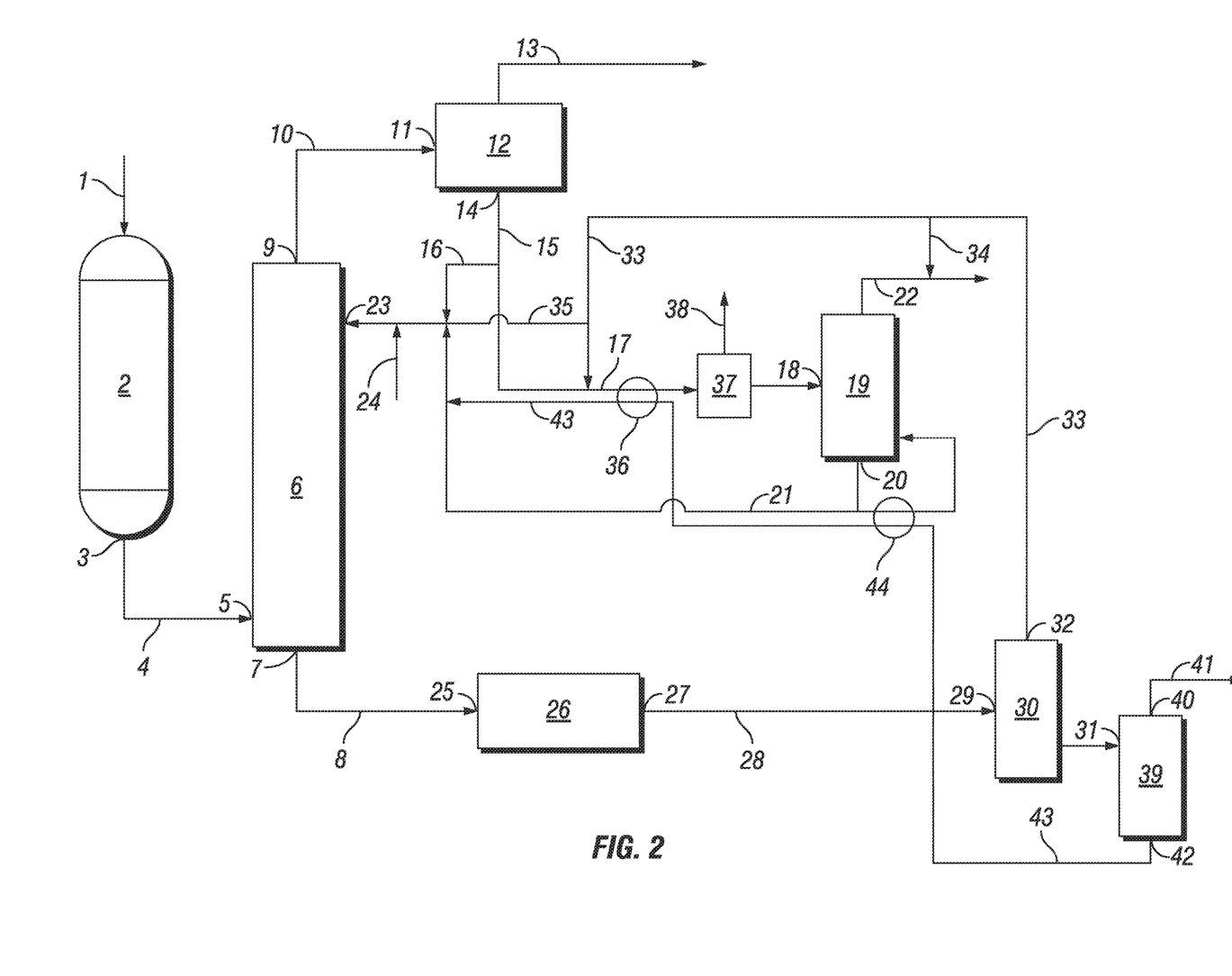

Reference is now made to FIGS. 1-2, which are schematic views of a reaction system for the production of ethylene carbonate and/or ethylene glycol, according to an embodiment of the present disclosure. It will be clear to the skilled person, that as schematic diagrams these figures do not show all necessary inputs, outputs, recycle streams, etc. that may be present in the reaction system. Furthermore, in the figures herein, as will be appreciated, elements can be added, exchanged, and/or eliminated so as to provide any number of additional embodiments and the sequence in which various feed components and/or streams are introduced into the process and their respective points of introduction, as well as the flow connections, may be varied from that depicted. In addition, as will be appreciated, the proportion and the relative scale of the elements provided in the figure are intended to illustrate the embodiments of the present disclosure, and should not be taken in a limiting sense.

The reaction system includes ethylene oxide reactor (2), which comprises an epoxidation catalyst. Epoxidation feed gas (1) is supplied to ethylene oxide reactor (2) via one or more inlets, and typically comprises ethylene, oxygen, ballast gas (e.g., methane or nitrogen), and a reaction modifier (e.g., monochloroethane, vinyl chloride or dichloroethane). In ethylene oxide reactor (2), ethylene is reacted with oxygen in the presence of an epoxidation catalyst to yield ethylene oxide product stream (4). Ethylene oxide product stream (4) exits ethylene oxide reactor (2) via an outlet, such as outlet (3), which is in fluid communication with a first inlet of absorber (6), such as inlet (5).

In absorber (6), the ethylene oxide product stream is brought into intimate contact with lean absorbent in the presence of one or more carboxylation and hydrolysis catalysts. At least a portion of, and preferably substantially all of, the ethylene oxide in the ethylene oxide product stream is absorbed into the lean absorbent. Fat absorbent stream (8), which comprises ethylene carbonate and/or ethylene glycol, is withdrawn from absorber (6) via a first outlet, such as outlet (7), while any gases not absorbed in absorber (6) are withdrawn via a second outlet, such as outlet (9), and condensed to yield overhead absorber stream (10).

Overhead absorber stream (10) is supplied to vapor-liquid separator (12) (such as a knock-out vessel, flash vessel, etc.) via an inlet, such as inlet (11), to yield recycle gas stream (13) and aqueous bottoms stream (15). Typically, at least a portion of recycle gas stream (13) is recycled back to ethylene oxide reactor (2), optionally after being supplied to a carbon dioxide absorption column and/or one or more guard beds (not shown).

Aqueous bottoms stream (15) is withdrawn from vapor-liquid separator (12) via an outlet, such as outlet (14) and supplied as aqueous process stream (17) to distillation apparatus (19) via an inlet, such as inlet (18), which is typically located near the upper middle portion of the column. Optionally, any portion of aqueous bottoms stream (15) that bypasses distillation apparatus (19) may be combined with purified aqueous process stream (21) via line (16) and supplied to absorber (6) via a second inlet, such as inlet (23).

The thermal energy needed for the operation of distillation apparatus (19) may be supplied by any suitable heating mechanism, such as a reboiler, and is preferably heated by using heat integration with a hot process stream, such as a catalyst recycle stream or a glycol absorbent stream. For example, as shown in FIG. 2, the thermal energy needed for the operation of distillation apparatus (19) is supplied by reboiler (44), which is heated by heat integration with hot process stream (43) withdrawn from separator (39).

Optionally, as shown in FIG. 2, before being supplied to distillation apparatus (19), aqueous process stream (17) may be supplied to a heating mechanism, such as preheater (36), and then to flash vessel (37) to recover light ends (e.g., ethylene and methane) as light ends stream (38), which is preferably recycled back to ethylene oxide reactor (2) after compression. Preferably, preheater (36) is similarly heated by heat integration with hot process stream (43) withdrawn from separator (39).

Overhead impurities stream (22) is withdrawn at or near the top portion of distillation apparatus (19) and is typically disposed of as waste. Purified aqueous process stream (21) is withdrawn from distillation apparatus (19) via an outlet, such as outlet (20), preferably located at or near the bottom portion of distillation apparatus (19), and is supplied to absorber (6) via inlet (23), for recirculation as lean absorbent. Make-up water (24) can be supplied if necessary.

Fat absorbent stream (8), which comprises ethylene carbonate and/or ethylene glycol, is optionally supplied to one or more finishing reactors, such as hydrolysis reactor (26), via an inlet, such as inlet (25) (e.g., to provide further conversion of any ethylene oxide and/or ethylene carbonate that was not converted in the ethylene oxide absorber). Finishing reactor product stream (28) is withdrawn from the one or more finishing reactors, such as hydrolysis reactor (26), via an outlet, such as outlet (27) and supplied to dehydrator (30) as a dehydrator feed stream via an inlet, such as inlet (29). In dehydrator (30), water is removed from the dehydrator feed stream to yield dehydrator bottom stream (31) comprising predominately MEG, and overhead dehydrator stream (33).

Overhead dehydrator stream (33) is withdrawn from dehydrator (30) via an outlet, such as outlet (32). Optionally, all or a portion of overhead dehydrator stream (33) may be combined with purified aqueous process stream (21) via line (35) and supplied to absorber (6) via inlet (23). Similarly, all or a portion of overhead dehydrator stream (33) may optionally be combined with aqueous bottoms stream (15) and supplied as aqueous process stream (17) to distillation apparatus (19), via inlet (18). Further, all or a portion of overhead dehydrator stream (33) may optionally be combined with overhead impurities stream (22) via line (34) and disposed of as waste water.

Dehydrator bottom stream (31) is withdrawn from dehydrator (30), typically at or near the bottom of dehydrator (30), and optionally supplied to a glycol purification apparatus (not shown) to separate glycols and remove impurities. As shown in FIG. 2, dehydrator bottom stream (31) may optionally be supplied to separator (39). Glycol product stream (41) is withdrawn from separator (39), via an outlet, such as outlet (40), and is optionally supplied to a glycol purification apparatus (not shown) to remove impurities. Further, hot process stream (43), such as a catalyst recycle stream or a glycol absorbent stream, is withdrawn from separator (39), via an outlet, such as outlet (42), and is preferably cooled and recycled to absorber (6) via inlet (23). As previously mentioned, the thermal energy needed for reboiler (44) and preheater (36) is preferably supplied via heat integration with hot process stream (43), such as a catalyst recycle stream or a glycol absorbent stream, withdrawn from separator (39).

That which is claimed is:

1. A process for the production of ethylene carbonate and/or ethylene glycol comprising:
    a) supplying an overhead absorber stream withdrawn from an absorber to a vapor-liquid separator to yield an aqueous bottoms stream and a recycle gas stream;
    b) supplying an aqueous process stream comprising one or more impurities to a distillation apparatus to yield an overhead impurities stream and a purified aqueous process stream;
    c) supplying at least a portion of the purified aqueous process stream and an ethylene oxide product stream to the absorber; and
    d) contacting the ethylene oxide product stream with the purified aqueous process stream in the absorber in the presence of one or more carboxylation and hydrolysis catalysts to yield a fat absorbent stream comprising ethylene carbonate and/or ethylene glycol.

2. The process according to claim 1 wherein the aqueous process stream supplied to the distillation apparatus comprises at least a portion of one or more streams selected from the group consisting of: the aqueous bottoms stream withdrawn from the vapor-liquid separator, an overhead dehydrator stream—withdrawn from a dehydrator, and a combination thereof.

3. The process according to claim 1, wherein the one or more impurities are selected from the group consisting of: formaldehyde, acetaldehyde, 2,3-epoxy-1,4-dioxane, 1,3-dioxolane, 1,4-dioxane, 2-methyl-1,3-dioxolane, 2-methoxy ethanol, 2,2'-bis-1,3-dioxolane, 2-chloro-methyl-1,3-dioxolane, 2-chloroethanol, and a combination thereof.

4. The process according to claim 1 further comprising: supplying the aqueous process stream to a preheater and a flash vessel prior to supplying the aqueous process stream to the distillation apparatus.

5. The process according to claim 4, wherein the preheater is heated via heat integration with a hot process stream withdrawn from a separator.

6. The process according to claim 1, wherein heat is supplied to the distillation apparatus using a reboiler, and wherein the reboiler is heated by heat integration with a hot process stream withdrawn from a separator.

7. The process according to claim 1 further comprising:
    e) supplying at least a portion of the fat absorbent stream to one or more finishing reactors to yield a finishing reactor product stream, and
    f) supplying at least a portion of the finishing reactor product stream to a dehydrator to yield a dehydrator bottom stream and an overhead dehydrator stream.

8. The process according to claim 7 further comprising:
    g) supplying at least a portion of the dehydrator bottom stream to a separator to yield a glycol product stream and a hot process stream; and
    h) supplying at least a portion of the hot process stream to the absorber.

* * * * *